(12) United States Patent
Schroeter et al.

(10) Patent No.: US 12,427,606 B2
(45) Date of Patent: Sep. 30, 2025

(54) SYSTEMS AND METHODS FOR NON-DESTRUCTIVELY TESTING STATOR WELD QUALITY AND EPOXY THICKNESS

(71) Applicant: Ford Global Technologies, LLC, Dearborn, MI (US)

(72) Inventors: Robert Schroeter, Livonia, MI (US); Michael Oelscher, Bergheim (DE)

(73) Assignee: Ford Global Technologies, LLC, Dearborn, MI (US)

( * ) Notice: Subject to any disclaimer, the term of this patent is extended or adjusted under 35 U.S.C. 154(b) by 381 days.

(21) Appl. No.: 18/172,643

(22) Filed: Feb. 22, 2023

(65) Prior Publication Data

US 2024/0278357 A1    Aug. 22, 2024

(51) Int. Cl.

| | |
|---|---|
| *B23K 31/12* | (2006.01) |
| *B23K 31/00* | (2006.01) |
| *G01N 21/88* | (2006.01) |
| *G01N 21/95* | (2006.01) |
| *G01N 33/44* | (2006.01) |
| *H02K 15/10* | (2006.01) |
| *H02K 15/33* | (2025.01) |
| *B23K 101/36* | (2006.01) |

(52) U.S. Cl.
CPC .......... *B23K 31/125* (2013.01); *B23K 31/006* (2013.01); *G01N 21/8851* (2013.01); *G01N 33/442* (2013.01); *H02K 15/105* (2013.01); *H02K 15/33* (2025.01); *B23K 2101/36* (2018.08); *G01N 2021/8854* (2013.01)

(58) Field of Classification Search
CPC ................ B23K 31/125; B23K 31/006; G01N 21/8851; G01N 21/95; G06T 7/0002
See application file for complete search history.

(56) References Cited

U.S. PATENT DOCUMENTS

| | | |
|---|---|---|
| 9,251,576 B2 * | 2/2016 | Von Berg .................. G06T 5/50 |
| 10,380,911 B2 * | 8/2019 | Hsu ........................ G09B 19/24 |
| 2013/0075371 A1 | 3/2013 | De Souza et al. |
| 2022/0126405 A1 * | 4/2022 | Maslar ................ B23K 31/006 |
| 2022/0244194 A1 | 8/2022 | Perron et al. |

FOREIGN PATENT DOCUMENTS

| | | | |
|---|---|---|---|
| WO | 2022056640 | 3/2022 | |
| WO | WO-2022056640 A1 * | 3/2022 | ......... G01N 29/0654 |

\* cited by examiner

*Primary Examiner* — Siamak Harandi
*Assistant Examiner* — Jaspreet Kaur
(74) *Attorney, Agent, or Firm* — Burris Law, PLLC (57) ABSTRACT

A method includes obtaining pre-weld image data of the electric motor stator from one or more image sensors; performing a welding process in response to obtaining the pre-weld image data, obtaining post-weld image data of the electric motor stator from the one or more image sensors in response to performing the welding process, obtaining epoxy image data of the electric motor stator from the one or more image sensors in response to obtaining the post-weld image data, performing a difference-based image processing routine based on the post-weld image data and the epoxy image data to generate a digital twin of the electric motor stator, and determining one or more epoxy characteristics of the electric motor stator based on the digital twin.

20 Claims, 7 Drawing Sheets

SYSTEMS AND METHODS FOR NON-DESTRUCTIVELY TESTING STATOR WELD QUALITY AND EPOXY THICKNESS

FIELD

The present disclosure relates to systems and methods for non-destructively testing stator weld quality and epoxy thickness.

BACKGROUND

The statements in this section merely provide background information related to the present disclosure and may not constitute prior art.

Weld quality and an insulation quality (e.g., an epoxy quality) of an electric motor stator are commonly assessed using destructive or non-destructive testing techniques. As an example, manual and visual inspections are performed to evaluate a weld quality, such as identifying the presence of cracks, voids, contamination discoloration, and/or other weld characteristics. Subsequently, a manual and visual inspection of the properties of the epoxy deposited thereon is performed to identify characteristics associated with the insulation quality. As another example, a vision system may employ image processing routines to evaluate the weld quality and the properties of the epoxy deposited thereon. However, conventional destructive and non-destructive testing techniques for evaluating the quality of the electric motor stator are time and resource intensive processes and are subject to, for example, incorrect evaluations (e.g., accepting defective welds or rejecting proper welds). These issues with destructive and non-destructive testing techniques, among other issues, are addressed by the present disclosure.

SUMMARY

This section provides a general summary of the disclosure and is not a comprehensive disclosure of its full scope or all of its features.

The present disclosure provides a method for non-destructively testing an electric motor stator. The method includes obtaining pre-weld image data of the electric motor stator from one or more image sensors; performing a welding process in response to obtaining the pre-weld image data, where the welding process includes welding hairpin wires and connectors of the electric motor stator; obtaining post-weld image data of the electric motor stator from the one or more image sensors in response to performing the welding process; obtaining epoxy image data of the electric motor stator from the one or more image sensors in response to obtaining the post-weld image data; performing a difference-based image processing routine based on the post-weld image data and the epoxy image data to generate a digital twin of the electric motor stator; and determining one or more epoxy characteristics of the electric motor stator based on the digital twin.

The following paragraph includes variations of the method of the above paragraph, and the variations may be implemented individually or in any combination.

In one variation, the method includes determining one or more pre-weld characteristics of the electric motor stator based on the pre-weld image data, and setting one or more parameters of the welding process based on the one or more pre-weld characteristics; the one or more pre-weld characteristics include a weld gap, a lateral offset, a vertical offset, a degradation characteristic, a trimming characteristic, or a combination thereof; the method includes performing a post-weld verification routine to determine one or more post-weld characteristics of the electric motor stator based on the post-weld image data, and selectively performing a post-weld corrective action based on the one or more post-weld characteristics; the one or more post-weld characteristics include a weld size, a weld shape, a weld alignment, a pore visibility, a discoloration, or a combination thereof; the difference-based image processing routine is a computer vision routine; performing the computer vision routine based on the post-weld image data and the epoxy image data to generate the digital twin of the electric motor stator further comprises: determining, for each pixel from among a plurality of pixels of the post-weld image data, a post-weld intensity value, determining, for each pixel from among a plurality of pixels of the epoxy image data, an epoxy intensity value, and determining, for each pixel from among the plurality of pixels of the epoxy image data, an intensity difference between the epoxy intensity value and a corresponding post-weld intensity value, where the digital twin is further based on the intensity difference associated with each pixel from among the plurality of pixels of the epoxy image data; the difference-based image processing routine is a convolutional neural network routine; performing the convolutional neural network routine based on the post-weld image data and the epoxy image data to generate the digital twin of the electric motor stator further comprises: aligning the post-weld image data and the epoxy image data based on a reference object of the electric motor stator, determining, in response to aligning the image data and the epoxy image data and for each pixel from among a plurality of pixels of the post-weld image data, a post-weld intensity value, determining, for each pixel from among a plurality of pixels of the epoxy image data, an epoxy intensity value, determining, for each pixel from among the plurality of pixels of the epoxy image data, an intensity difference between the epoxy intensity value and a corresponding post-weld intensity value, generating the digital twin based on the intensity difference associated with each pixel from among the plurality of pixels of the epoxy image data; the method further comprises providing the digital twin to one or more convolutional layers to generate one or more feature maps, and providing the one or more feature maps to one or more pooling layers to generate a reduced image, where the one or more epoxy characteristics are further based on the reduced image; and/or the one or more epoxy characteristics include an epoxy thickness, an epoxy distribution, or a combination thereof.

The present disclosure provides another method for non-destructively testing an electric motor stator. The method includes obtaining pre-weld image data of the electric motor stator from one or more image sensors; determining one or more pre-weld characteristics of the electric motor stator based on the pre-weld image data; performing a welding process based on the one or more pre-weld characteristics, where the welding process includes welding hairpin wires and connectors of the electric motor stator; obtaining post-weld image data of the electric motor stator from the one or more image sensors in response to performing the welding process; obtaining epoxy image data of the electric motor stator from the one or more image sensors in response to obtaining the post-weld image data; performing a difference-based image processing routine based on the post-weld image data and the epoxy image data to generate a digital twin of the electric motor stator; and determining one or more epoxy characteristics of the electric motor stator based on the digital twin.

The following paragraph includes variations of the method of the above paragraph, and the variations may be implemented individually or in any combination.

In one variation, the one or more pre-weld characteristics include a weld gap, a lateral offset, a vertical offset, a degradation characteristic, a trimming characteristic, or a combination thereof; the method includes performing a post-weld verification routine to determine one or more post-weld characteristics of the electric motor stator based on the post-weld image data, and selectively performing a post-weld corrective action based on the one or more post-weld characteristics, where the one or more post-weld characteristics include a weld size, a weld shape, a weld alignment, a pore visibility, a discoloration, or a combination thereof; performing the difference-based image processing routine based on the post-weld image data and the epoxy image data to generate the digital twin of the electric motor stator further comprises: determining, for each pixel from among a plurality of pixels of the post-weld image data, a post-weld intensity value, determining, for each pixel from among a plurality of pixels of the epoxy image data, an epoxy intensity value, determining, for each pixel from among the plurality of pixels of the epoxy image data, an intensity difference between the epoxy intensity value and a corresponding post-weld intensity value, where the digital twin is further based on the intensity difference associated with each pixel from among the plurality of pixels of the epoxy image data; the difference-based image processing routine is a computer vision routine; the difference-based image processing routine is a convolutional neural network routine, and where the method further comprises: aligning the post-weld image data and the epoxy image data based on a reference object of the electric motor stator, determining, in response to aligning the image data and the epoxy image data and for each pixel from among the plurality of pixels of the post-weld image data, the post-weld intensity value, providing the digital twin to one or more convolutional layers to generate one or more feature maps, and providing the one or more feature maps to one or more pooling layers to generate a reduced image, where the one or more epoxy characteristics are further based on the reduced image; and/or the one or more epoxy characteristics include an epoxy thickness, an epoxy distribution, or a combination thereof.

The present disclosure provides a system for non-destructively testing an electric motor stator. The system includes one or more processors and one or more nontransitory computer-readable mediums comprising instructions that are executable by the one or more processors. The instructions include obtaining pre-weld image data of the electric motor stator from one or more image sensors; determining one or more pre-weld characteristics of the electric motor stator based on the pre-weld image data; performing a welding process based on the one or more pre-weld characteristics, where the welding process includes welding hairpin wires and connectors of the electric motor stator; obtaining post-weld image data of the electric motor stator from the one or more image sensors in response to performing the welding process; obtaining epoxy image data of the electric motor stator from the one or more image sensors in response to obtaining the post-weld image data; performing a difference-based image processing routine based on the post-weld image data and the epoxy image data to generate a digital twin of the electric motor stator; and determining one or more epoxy characteristics of the electric motor stator based on the digital twin, where the one or more epoxy characteristics include an epoxy thickness, an epoxy distribution, or a combination thereof.

The following paragraph includes variations of the system of the above paragraph, and the variations may be implemented individually or in any combination.

In one variation, the difference-based image processing routine is one of a computer vision routine and a convolutional neural network routine.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 1A:
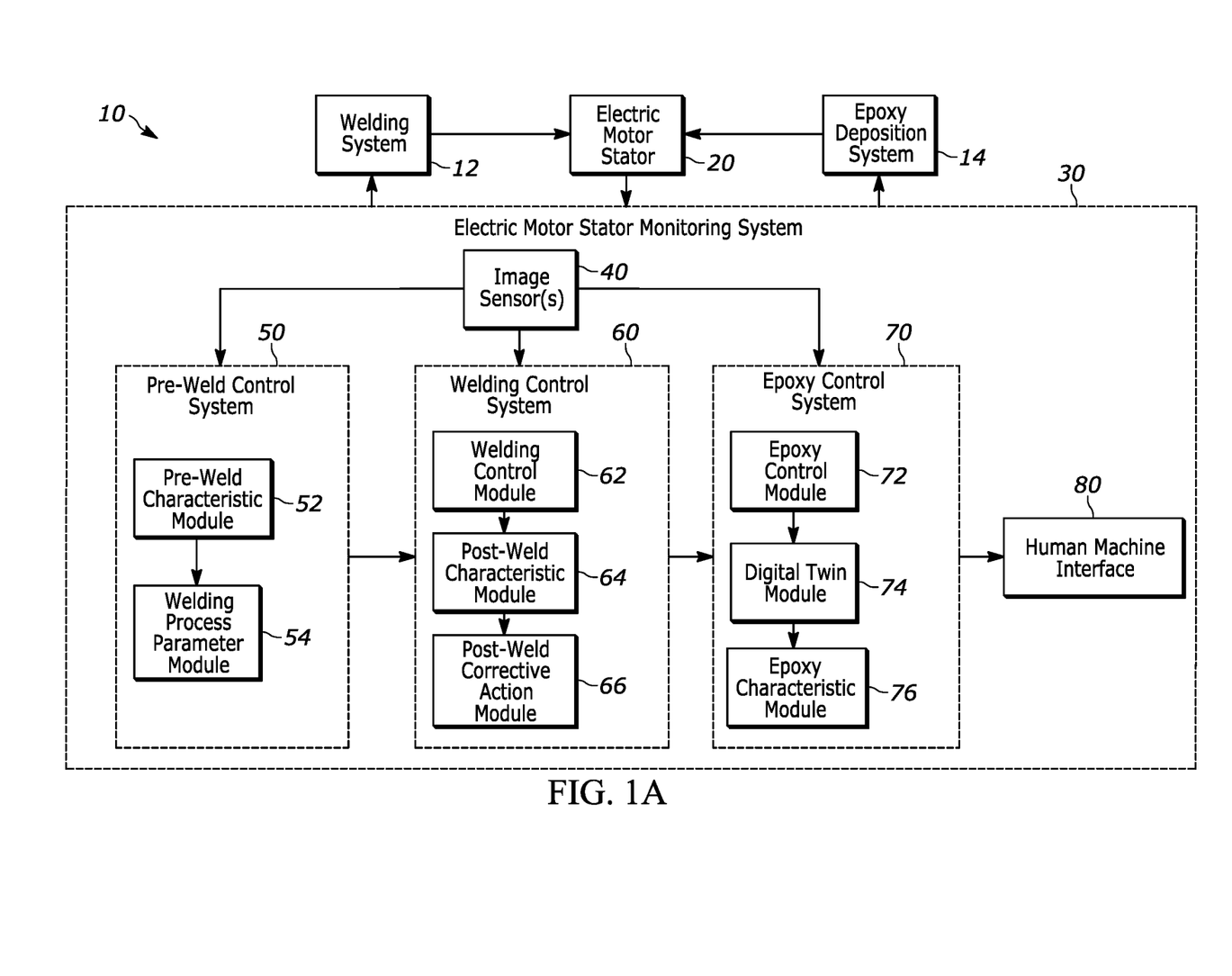
FIG. 1A is a block diagram of an example electric motor stator fabrication environment in accordance with the teachings of the present disclosure.
Figure 1B:
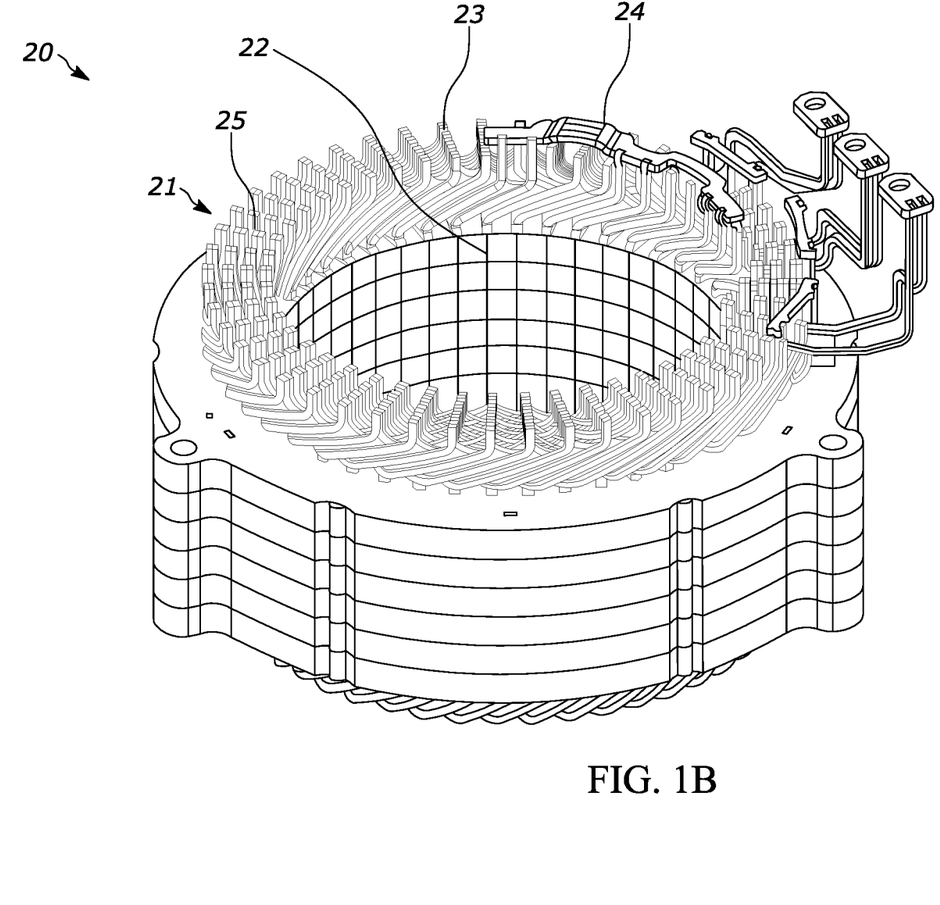
FIG. 1B schematically illustrates an electric motor stator in accordance with the teachings of the present disclosure.

Referring to FIGS. 1A-1B, an electric motor stator fabrication environment 10 is shown and generally includes a welding system 12, an epoxy deposition system 14, an electric motor stator 20, and an electric motor stator monitoring system 30. The electric motor stator monitoring system 30 includes one or more image sensors 40, a pre-weld control system 50, a welding control system 60, an epoxy control system 70, and a human machine interface (HMI) 80. In one form, the one or more image sensors 40, the pre-welding control system 50, the welding control system 60, the epoxy control system 70, and the HMI 80 are communicably coupled using a wired and/or wireless communication protocol (e.g., a Bluetooth®-type protocol, a cellular protocol, a wireless fidelity (Wi-Fi)-type protocol, a near-field communication (NFC) protocol, an ultra-wideband (UWB) protocol, among others).

In one form, the electric motor stator 20 includes a stator winding 21 and a stator core 22. The stator winding 21 is formed by a plurality of hairpin wires 23 electrically connected (e.g., welded) to each other and electrically connected to connectors 24. The hairpin wires are made from copper or a copper alloys, and the stator core 22 is made from a metal or alloy, such as steel. Each of the hairpin wires 23 is bent or formed in a desired shape after insertion into and through the stator core 22 and have an epoxy 25 (e.g., a protective enamel coating, such as a multi-layer PA-PIA, PEEK, or other polymer coating) to electrically insulate the hairpin wires 23 from the stator core 22. Furthermore, the epoxy 25 is removed from or not present at ends of the hairpin wires 23 (i.e., the ends are "de-coated"), and hairpin wire pairs or hairpin wire-connector pairs are joined (e.g., welded) together to form a desired stator winding and for an electric motor. The hairpin wire pairs and the hairpin wire-connector pairs are typically welded together to provide connections (i.e., welds) with low electrical resistivity, desired static strength, resistance to fatigue stresses (both vibrational and thermal) and consistent, low discontinuity metallurgical properties.

In one form, the welding system 12 is configured to perform a welding process on the electric motor stator 20 by welding the hairpin wire pairs and the hairpin wire-connector pairs. As an example, the welding system 12 is employed by a laser welding system having a laser source (e.g., 6 kW Trumpf TruDisk laser (1035 nm) with a Trumpf PFO-33 optic) and a fiber (e.g., a Trumpf Brightline 50/200 um core ring fiber) that are collectively configured to perform the welding process. It should be understood that the welding system 12 may be provided by other types of welding systems and is not limited to the laser welding system described herein.

In one form, the epoxy deposition system 14 is configured to perform an epoxy deposition process on the electric motor stator 20 by depositing a protective epoxy coating on the hairpin wires 23. Accordingly, depositing the epoxy 25 may electrically insulate the stator core 22 from the hairpin wires 23. As an example, the epoxy deposition system 14 is employed by a time-pressure epoxy deposition system, an auger, a jetting epoxy deposition system, among other types of epoxy deposition systems. As described above, the epoxy deposition process includes de-coating the epoxy 25 at ends of the hairpin wires 23 to thereby form the desired stator windings.

In one form, the one or more image sensors 40 are configured to obtain image data of the electric motor stator 20. The one or more image sensors 40 may include, but are not limited to, a two-dimensional (2D) camera, a three-dimensional (3D) camera, an optical sensor, or a scanner device (e.g., a radar scanner, a laser scanner, a light detection and ranging (LIDAR) sensor, an ultrasonic sensor, an infrared sensor, among other scanner devices), a light digitizer, and/or a digital micrometer. In one form, the one or more image sensors 40 are configured to obtain pre-weld image data, post-weld image data, and epoxy image data. As used herein, "pre-weld image data" refers to image data of the electric motor stator 20 prior to a welding process being performed (e.g., prior to welding the hairpin wires 23). As used herein, "post-weld image data" refers to image data of the electric motor stator 20 after a welding process has been completed (e.g., after welding the hairpin wires 23) and prior to the epoxy coating/deposition process. That is, the post-weld image data may be obtained in response to (e.g., after) obtaining the pre-weld image data and/or performing the welding process. As used herein, "epoxy image data" refers to image data of the electric motor stator 20 after a welding process and an epoxy coating/deposition process have been completed (e.g., after welding the hairpin wires 23 and depositing the epoxy 25 on the hairpin wires 23). That is, the epoxy image data may be obtained in response to (e.g., after) obtaining the post-weld image data.

Figure 2A:
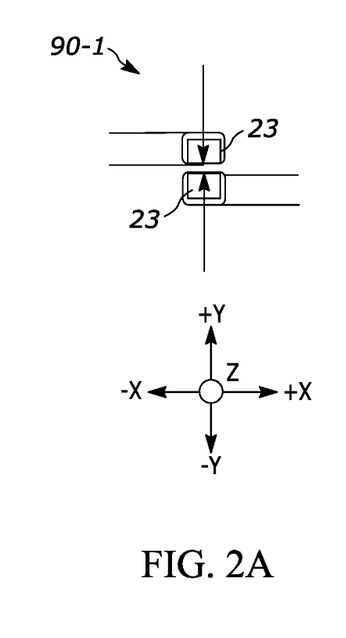
FIG. 2A illustrates a weld gap in accordance with the teachings of the present disclosure.
Figure 2B:
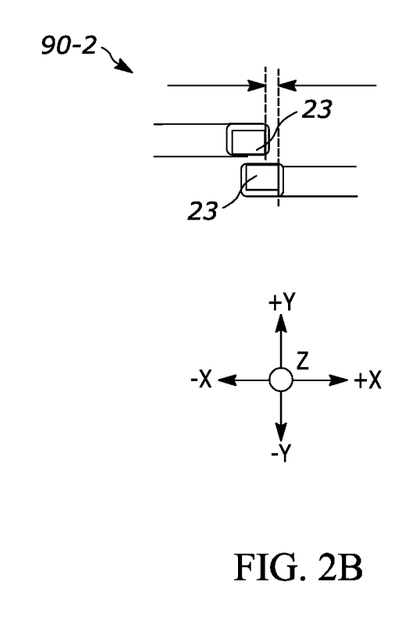
FIG. 2B illustrates a lateral offset in accordance with the teachings of the present disclosure.
Figure 2C:
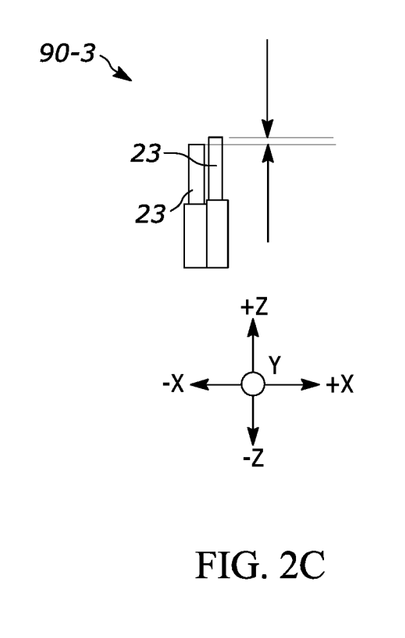
FIG. 2C illustrates vertical offset in accordance with the teachings of the present disclosure.

In one form, the pre-welding control system 50 includes a pre-weld characteristic module 52 and a welding process parameter module 54. The pre-weld characteristic module 52 determines one or more pre-weld characteristics of the electric motor stator 20 based on the pre-weld image data. As an example, the one or more pre-weld characteristics include a weld gap, a lateral offset, a vertical offset, a degradation characteristic, a trimming characteristic, or a combination thereof. As used herein and as shown in FIG. 2A, the "weld gap" refers to a distance between a pair of hairpin wires 23 in a longitudinal direction (i.e., +Y direction), as shown by image 90-1 in FIG. 2A. As used herein and as shown by image 90-2 in FIG. 2B, the "lateral offset" refers to a distance between a pair of hairpin wires 23 in a lateral direction (i.e., +X direction). As used herein and as shown by image 90-3 in FIG. 2C, the "vertical offset" refers to a distance between a pair of hairpin wires 23 in a vertical direction (i.e., +Z direction). As used herein, "degradation characteristic" refers to a quantitative or qualitative representation of an amount of degradation of the hairpin wires 23 caused by, for example, physical deformations and/or chemical reactions (e.g., an amount of removal or contamination of an enamel insulative layer of the hairpin wires 23). As used herein, "trimming characteristic" refers to one or more characteristics of the hairpin wires 23 resulting from a trimming operation performed on the hairpin wires 23, such as a presence of voids, pits, and/or cracks within the hairpin wires 23.

To perform the functionality described herein, the pre-weld characteristic module 52 may be configured to perform known image processing routines to identify the one or more pre-weld characteristics, such as a computer vision routine or a machine learning routine. As an example, the pre-weld characteristic module 52 is employed by a convolutional neural network having one or more convolutional layers and one or more pooling layers. The one or more convolutional layers may be iteratively trained using known training routines to define, for example, the kernel dimensions, number of kernels, stride values, padding values, input/output channels, bit depths, feature map widths/lengths, weights and/or rectified linear unit (ReLU) activation layers therein. Furthermore, the one or more pooling layers may be iteratively trained using known training routines to define, for example, a type of pooling routine (e.g., a maximum pooling routine, an average pooling routine, an L2-norm pooling routine, among other pooling routines), kernel dimensions, and sliding values.

In one form, the welding process parameter module 54 is configured to define one or more parameters of the welding process performed by the welding system 12. As an example, the welding process parameter module 54 may selectively adjust one or more parameters of the welding process to accommodate or mitigate deviations of the one or more of the pre-weld characteristics (i.e., a weld gap, a lateral offset, a vertical offset, a degradation characteristic, and/or a trimming characteristic) from a nominal value or range.

In one form, the welding control system 60 includes a welding control module 62, a post-weld characteristic module 64, and a post-weld corrective action module 66. The welding control module 62 controls the welding process performed by the welding system 12 based on the one or more parameters defined by the welding process parameter module 54, as described above. The post-weld characteristic module 64 performs a post-weld verification routine to determine one or more post-weld characteristics of the electric motor stator 20 based on the post-weld image data. Example post-weld characteristics include, but are not limited to, a weld size (e.g., a volume, cross-sectional area, surface area, etc.), a weld shape, a weld alignment (e.g., a vertical, horizontal, and/or lateral alignment), a pore visibility, a discoloration (e.g., a defect discoloration resulting from contamination) or a combination thereof. To perform the functionality described herein, the post-weld characteristic module 64 may perform known image processing routines to identify the one or more post-weld characteristics, such as a computer vision routine or a machine learning routine. As an example, the post-weld characteristic module 64 is employed by a convolutional neural network having one or more convolutional layers and one or more pooling layers. Example convolutional neural networks for determining a post-weld characteristic are disclosed in U.S. patent Ser. No. 17/078,758 titled "AUTOMATED INSPECTION AND VERIFICATION OF ELECTRIC MOTOR WELD QUALITY," which is commonly owned with the present application and the contents of which are incorporated herein by reference in its entirety.

Figure 2D:
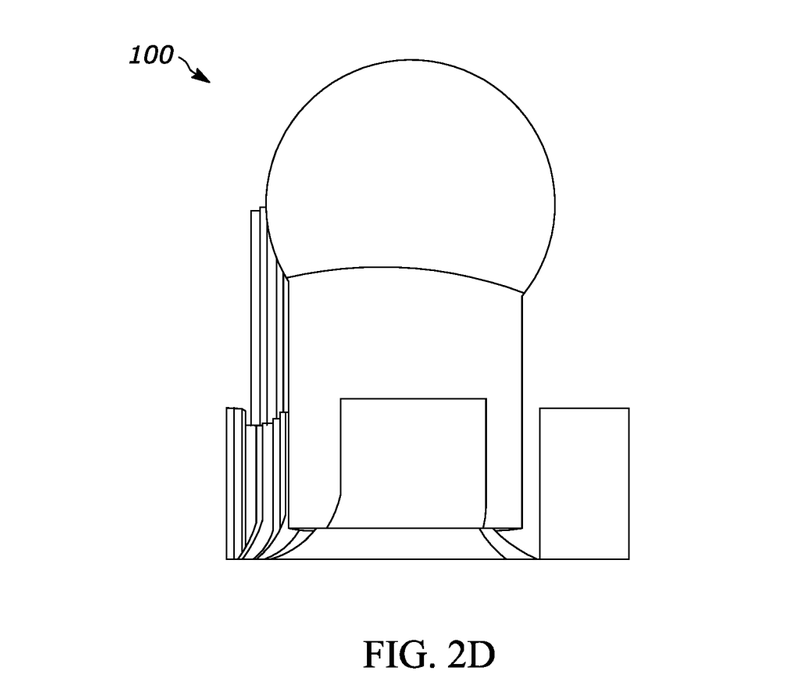
FIG. 2D illustrates an example digital twin of the electric motor stator in accordance with the teachings of the present disclosure.

In one form, the epoxy control system 70 includes an epoxy control module 72, a digital twin module 74, and an epoxy characteristic module 76. The epoxy control module 72 controls the epoxy deposition process performed by the epoxy deposition system 14. The digital twin module 74 obtains the epoxy image data and performs a difference-based image processing routine based on the post-weld image data and the epoxy image data to generate a digital twin of the electric motor stator 20. As an example and as shown in FIG. 2D, the digital twin module 74 performs a computer vision routine or a convolutional neural network routine to generate a digital twin 100 of the electric motor stator 20.

Figure 3:
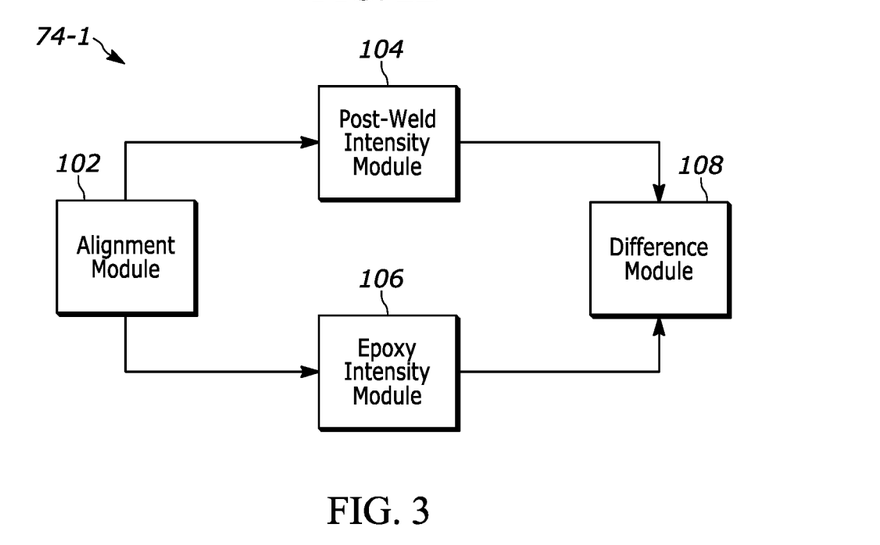
FIG. 3 illustrates an example digital twin module in accordance with the teachings of the present disclosure.

As an example and referring to FIG. 3, digital twin module 74-1 (as the digital twin module 74) is configured to perform a computer vision routine and includes an alignment module 102, a post-weld intensity module 104, an epoxy intensity module 106, and a difference module 108. In one form, the alignment module 102 is configured to align the pixel data of the post-weld image data and the pixel data of the epoxy image data based on a reference object of the electric motor stator 20 (e.g., a predetermined hairpin wire 23 or other component of the electric motor stator 20). That is, the alignment module 102 is configured to perform known image rotation, image translation, and image overlaying routines to overlay the epoxy image data onto the post-weld image data such that the pixel coordinates of the epoxy and post-weld image data correspond to each other.

When the epoxy and post-weld image data are aligned, the post-weld intensity module 104 determines a post-weld intensity value for each pixel of the post-weld image data, and the epoxy intensity module 106 determines an epoxy intensity value for each pixel of the epoxy image data. In one form, each intensity values is represented by one or more integers that correspond to a color. As an example, the intensity values may each be provided by a single integer between 0 and 255 when the epoxy and post-weld image data are grayscale images, where values of 0 correspond to a black color, and 255 corresponds to a white color. As another example, the intensity values may each be provided by three integers that are each between 0 and 255 when the epoxy and post-weld image data are color images, where each value corresponds to an amount of red light, blue light, and green light (e.g., RGB values).

In one form, the difference module 108 is configured to perform the difference-based image processing routine and generate the digital twin 100 by determining a difference between the post-weld intensity value and epoxy intensity value for each pixel. By performing the difference-based image processing routine (e.g., a pixel value subtraction routine), the difference module 108 is configured to "filter" or remove the features corresponding to the welds of the hairpin wires 23 and generate the digital twin 100 such that is indicative of the deposited epoxy of the electric motor stator 20. As described below in further detail, the epoxy characteristic module 76 is configured to determine one or more epoxy characteristics based on the digital twin 100.

Figure 4:
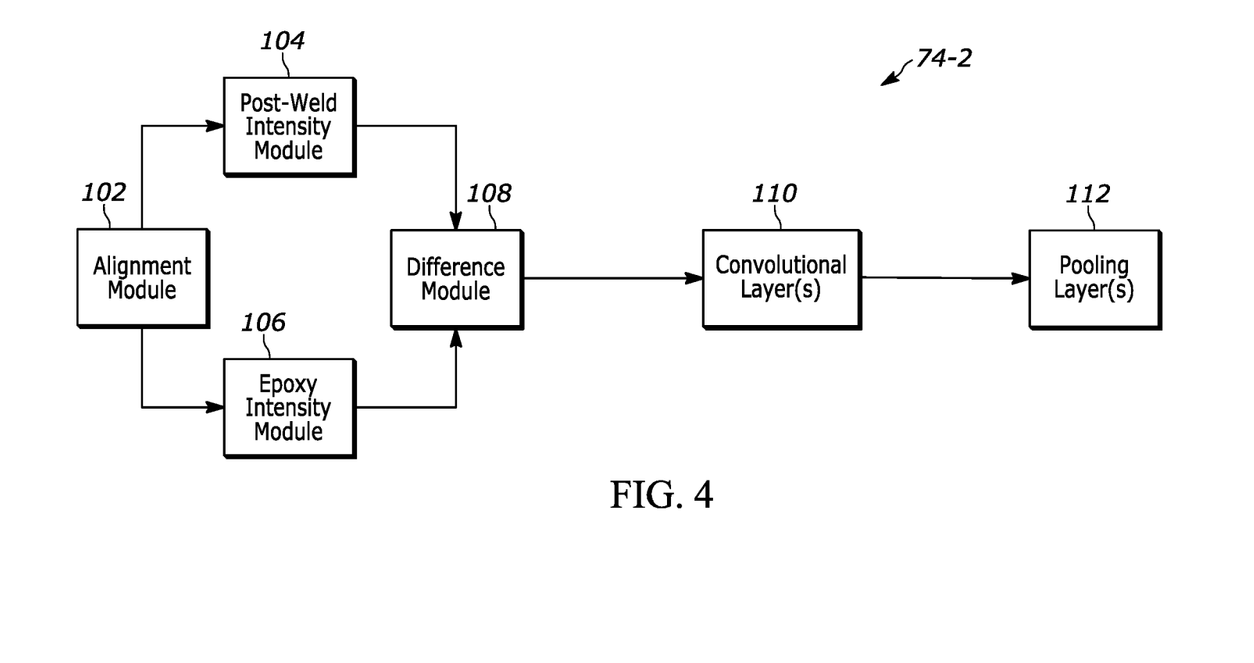
FIG. 4 illustrates another example digital twin module in accordance with the teachings of the present disclosure.

As another example and referring to FIG. 4, digital twin module 74-2 (as the digital twin module 74) is configured to perform a convolutional neural network routine and includes the alignment module 102, the post-weld intensity module 104, the epoxy intensity module 106, the difference module 108, one or more convolutional layers 110, and one or more pooling layers 112. As described above, the alignment module 102, the post-weld intensity module 104, the epoxy intensity module 106, and the difference module 108 collectively generate the digital twin 100 such that is indicative of the deposited epoxy of the electric motor stator 20.

Additionally, the difference module 108 provides the digital twin 100 to the one or more convolutional layers 110, which are configured to generate one or more feature maps based on the digital twin 100. The one or more convolutional layers 110 may be defined by any suitable combination of parameters, such as kernel dimensions, number of kernels, stride values, padding values, input/output channels, bit depths, feature map widths/lengths, and ReLU activation layers. As an example implementation of the one or more convolutional layers 110, a kernel (e.g., a 4×4 kernel) may be iteratively applied to the digital twin 100 in accordance with a defined stride (e.g., a stride value of 2). During each iteration, the one or more convolutional layers 110 perform a convolution routine (e.g., a scalar product routine) based on a set of pixels of the digital twin 100 in which the kernel is overlayed. The result of the convolution function at each iteration is output as a pixel value in a feature map.

In one form, the one or more convolutional layers 110 provide the feature maps to the one or more pooling layers 112 to generate a reduced image. That is, the one or more pooling layers 112 are configured to reduce the width and/or length of the feature maps and may be defined by various suitable parameters, such as a type of pooling routine (e.g., a maximum pooling routine, an average pooling routine, an L2-norm pooling routine, among other pooling routines), kernel dimensions, and sliding values. As an example, the one or more pooling layers 112 may be provided by one or more maximum pooling layers having a 2×2 kernel and a stride value of 1.

In one form, the epoxy characteristic module 76 determines the one or more epoxy characteristics of the electric motor stator 20 based on the digital twin 100. As an example, when the digital twin module 74 performs a convolutional neural network routine, the epoxy characteristic module 76 determines the one or more epoxy characteristics of the electric motor stator 20 based on the reduced images of the digital twin 100. As another example, when the digital twin module 74 performs a computer vision routine, the epoxy characteristic module 76 determines the one or more epoxy characteristics of the electric motor stator 20 based on the digital twin 100. To perform the functionality described herein, the epoxy characteristic module 76 may be configured to perform known image processing routines to identify the epoxy characteristics, such as a computer vision routine or a machine learning routine. As an example, the epoxy characteristic module 76 is employed by a convolutional neural network having one or more convolutional layers and one or more pooling layers that are collectively trained to detect the epoxy characteristics based on the digital twin 100 or, more specifically, the reduced image of the digital twin 100.

In one form, the one or more epoxy characteristics include an epoxy thickness, an epoxy distribution, or a combination thereof. As used herein, "epoxy thickness" refers to a thickness of the epoxy 25, and the thickness may be an average thickness, a minimum thickness, a maximum thickness, or other arithmetic representations of the thickness of the epoxy 25. As used herein, "epoxy distribution" refers to a qualitative of quantitative representation of the geometry, shape, or thickness uniformity of the epoxy 25. As an example, the epoxy distribution may indicate that certain portions of the epoxy 25 are below a nominal thickness. It should be understood that the epoxy characteristics may include any other type of characteristic associated with the epoxy 25 and is not limited to the examples described herein.

In one form, the HMI 80 includes an input device (e.g., a keyboard, mouse, among other input devices), a graphical user interface (e.g., a touchscreen display or other type of display device), and/or other types of HMIs configured to receive inputs from an operator. The HMI 80 may display at least one of the pre-weld characteristics, the post-weld characteristics, the epoxy characteristics, the digital twin 100, and/or the reduced images of the digital twin 100. Additionally, the HMI 80 may selectively broadcast an alert/notification when, for example, at least one of the pre-weld characteristics, the post-weld characteristics, and the epoxy characteristics deviate from a nominal value, as described herein. As another example, the HMI 80 may provide instructions for adjusting one or more parameters of the welding process and/or the epoxy deposition process to accommodate or mitigate deviations from nominal welding characteristics and epoxy characteristics, respectively.

Figure 5:
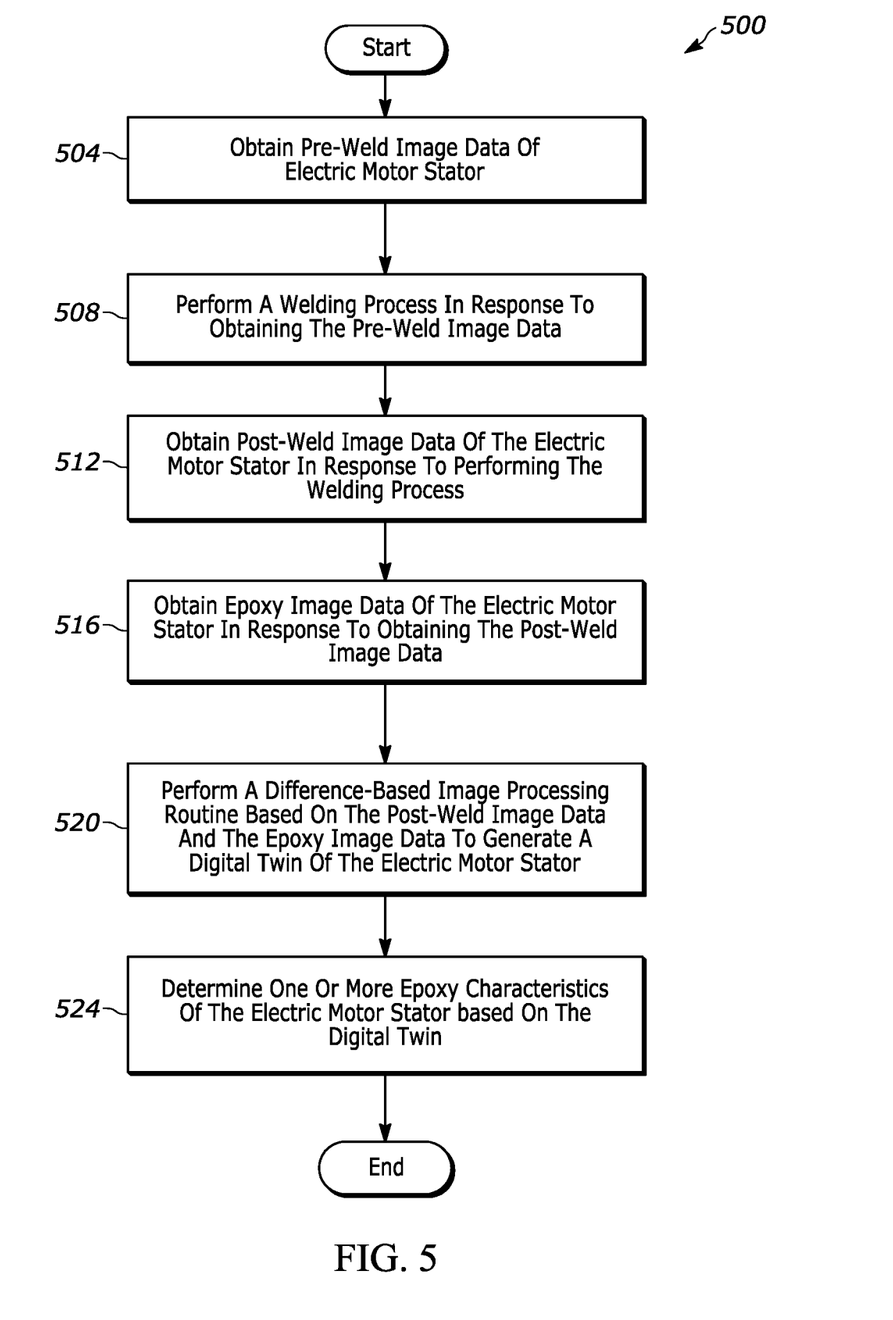
FIG. 5 is a flowchart illustrating an example routine for non-destructively testing an electric motor stator in accordance with the teachings of the present disclosure.

Referring to FIG. 5, a flowchart illustrating an example routine 500 for non-destructively testing the electric motor stator 20 is shown. At 504, the electric motor stator monitoring system 30 obtains pre-weld image data of the electric motor stator 20. At 508, the welding system 12 performs a welding process in response to the electric motor stator monitoring system 30 obtaining the pre-weld image data. At 512, the electric motor stator monitoring system 30 obtains post-weld image data of the electric motor stator 20 in response to performing the welding process. At 516, the electric motor stator monitoring system 30 obtains epoxy image data of the electric motor stator 20 in response to obtaining the post-weld image data. At 520, the electric motor stator monitoring system 30 performs a difference-based image processing routine based on the post-weld image data and the epoxy image data to generate the digital twin 100 of the electric motor stator 20. At 524, the electric motor stator monitoring system 30 determines one or more epoxy characteristics of the electric motor stator 20 based on the digital twin 100.

Figure 6:
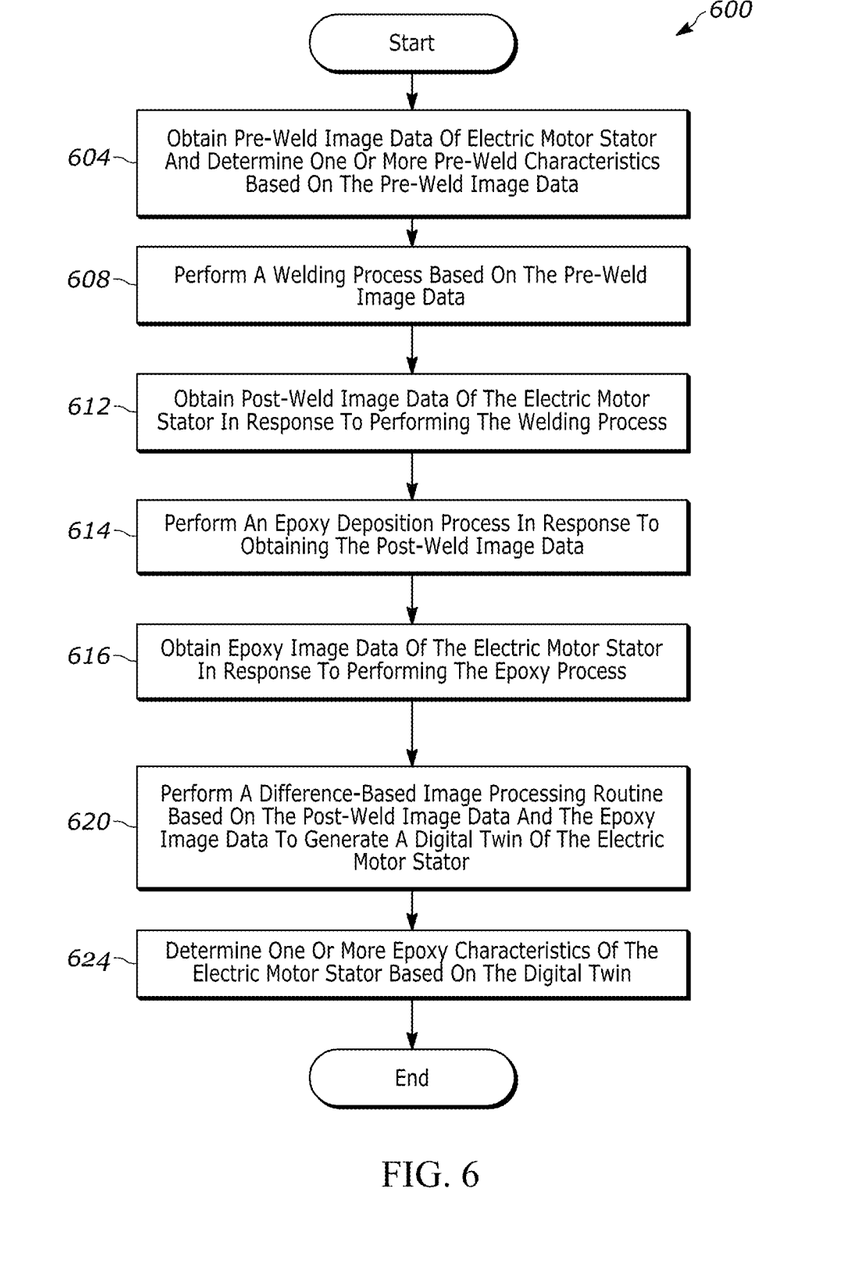
FIG. 6 is a flowchart illustrating another example routine for non-destructively testing an electric motor stator in accordance with the teachings of the present disclosure.

Referring to FIG. 6, a flowchart illustrating another example routine 600 for non-destructively testing the electric motor stator 20 is shown. At 604, the electric motor stator monitoring system 30 obtains pre-weld image data of the electric motor stator 20 and determines one or more pre-weld characteristics based on the pre-weld image data. At 608, the welding system 12 performs a welding process in response to the electric motor stator monitoring system 30 obtaining the pre-weld image data. At 612, the electric motor stator monitoring system 30 obtains post-weld image data of the electric motor stator 20 in response to performing the welding process. At 614, the epoxy deposition system 14 performs the epoxy deposition process in response to obtaining the post-weld image data. At 616, the electric motor stator monitoring system 30 obtains epoxy image data of the electric motor stator 20 in response to obtaining the post-weld image data and in response to performing the epoxy deposition process. At 620, the electric motor stator monitoring system 30 performs a difference-based image processing routine based on the post-weld image data and the epoxy image data to generate the digital twin 100 of the electric motor stator 20. At 624, the electric motor stator monitoring system 30 determines one or more epoxy characteristics of the electric motor stator 20 based on the digital twin 100.

Accordingly, the present disclosure provides systems and methods for non-destructively testing the electric motor stator 20. That is, by sequentially obtaining the pre-weld image data, post-weld image data, and epoxy image data and performing the image processing routines described herein, various characteristics of the hairpin wires 23 and the epoxy 25 can be monitored with improved accuracy without destructively testing the electric motor stator 20.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

In this application, the term "controller" and/or "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components (e.g., op amp circuit integrator as part of the heat flux data module) that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method for non-destructively testing an electric motor stator, the method comprising:
   obtaining pre-weld image data of the electric motor stator from one or more image sensors;
   performing a welding process in response to obtaining the pre-weld image data, wherein the welding process includes welding hairpin wires and connectors of the electric motor stator;
   obtaining post-weld image data of the electric motor stator from the one or more image sensors in response to performing the welding process;
   obtaining epoxy image data of the electric motor stator from the one or more image sensors in response to obtaining the post-weld image data;
   performing a difference-based image processing routine based on the post-weld image data and the epoxy image data to generate a digital twin of the electric motor stator; and
   determining one or more epoxy characteristics of the electric motor stator based on the digital twin.

2. The method of claim 1 further comprising:
   determining one or more pre-weld characteristics of the electric motor stator based on the pre-weld image data; and
   setting one or more parameters of the welding process based on the one or more pre-weld characteristics.

3. The method of claim 2, wherein the one or more pre-weld characteristics include a weld gap, a lateral offset, a vertical offset, a degradation characteristic, a trimming characteristic, or a combination thereof.

4. The method of claim 1 further comprising:
   performing a post-weld verification routine to determine one or more post-weld characteristics of the electric motor stator based on the post-weld image data; and
   selectively performing a post-weld corrective action based on the one or more post-weld characteristics.

5. The method of claim 4, wherein the one or more post-weld characteristics include a weld size, a weld shape, a weld alignment, a pore visibility, a discoloration, or a combination thereof.

6. The method of claim 1, wherein the difference-based image processing routine is a computer vision routine.

7. The method of claim 6, wherein performing the computer vision routine based on the post-weld image data and the epoxy image data to generate the digital twin of the electric motor stator further comprises:
   determining, for each pixel from among a plurality of pixels of the post-weld image data, a post-weld intensity value;
   determining, for each pixel from among a plurality of pixels of the epoxy image data, an epoxy intensity value; and
   determining, for each pixel from among the plurality of pixels of the epoxy image data, an intensity difference between the epoxy intensity value and a corresponding post-weld intensity value, wherein the digital twin is further based on the intensity difference associated with each pixel from among the plurality of pixels of the epoxy image data.

8. The method of claim 1, wherein the difference-based image processing routine is a convolutional neural network routine.

9. The method of claim 8, wherein performing the convolutional neural network routine based on the post-weld image data and the epoxy image data to generate the digital twin of the electric motor stator further comprises:
   aligning the post-weld image data and the epoxy image data based on a reference object of the electric motor stator;
   determining, in response to aligning the image data and the epoxy image data and for each pixel from among a plurality of pixels of the post-weld image data, a post-weld intensity value;
   determining, for each pixel from among a plurality of pixels of the epoxy image data, an epoxy intensity value;
   determining, for each pixel from among the plurality of pixels of the epoxy image data, an intensity difference between the epoxy intensity value and a corresponding post-weld intensity value; and
   generating the digital twin based on the intensity difference associated with each pixel from among the plurality of pixels of the epoxy image data.

10. The method of claim 9 further comprising:
    providing the digital twin to one or more convolutional layers to generate one or more feature maps; and
    providing the one or more feature maps to one or more pooling layers to generate a reduced image, wherein the one or more epoxy characteristics are further based on the reduced image.

11. The method of claim 1, wherein the one or more epoxy characteristics include an epoxy thickness, an epoxy distribution, or a combination thereof.

12. A method for non-destructively testing an electric motor stator, the method comprising:
    obtaining pre-weld image data of the electric motor stator from one or more image sensors;
    determining one or more pre-weld characteristics of the electric motor stator based on the pre-weld image data;
    performing a welding process based on the one or more pre-weld characteristics, wherein the welding process includes welding hairpin wires and connectors of the electric motor stator;
    obtaining post-weld image data of the electric motor stator from the one or more image sensors in response to performing the welding process;

obtaining epoxy image data of the electric motor stator from the one or more image sensors in response to obtaining the post-weld image data;

performing a difference-based image processing routine based on the post-weld image data and the epoxy image data to generate a digital twin of the electric motor stator; and determining one or more epoxy characteristics of the electric motor stator based on the digital twin.

13. The method of claim 12, wherein the one or more pre-weld characteristics include a weld gap, a lateral offset, a vertical offset, a degradation characteristic, a trimming characteristic, or a combination thereof.

14. The method of claim 12 further comprising:

performing a post-weld verification routine to determine one or more post-weld characteristics of the electric motor stator based on the post-weld image data; and selectively performing a post-weld corrective action based on the one or more post-weld characteristics, wherein the one or more post-weld characteristics include a weld size, a weld shape, a weld alignment, a pore visibility, a discoloration, or a combination thereof.

15. The method of claim 12, wherein performing the difference-based image processing routine based on the post-weld image data and the epoxy image data to generate the digital twin of the electric motor stator further comprises:

determining, for each pixel from among a plurality of pixels of the post-weld image data, a post-weld intensity value;

determining, for each pixel from among a plurality of pixels of the epoxy image data, an epoxy intensity value; and determining, for each pixel from among the plurality of pixels of the epoxy image data, an intensity difference between the epoxy intensity value and a corresponding post-weld intensity value, wherein the digital twin is further based on the intensity difference associated with each pixel from among the plurality of pixels of the epoxy image data.

16. The method of claim 15, wherein the difference-based image processing routine is a computer vision routine.

17. The method of claim 15, wherein the difference-based image processing routine is a convolutional neural network routine, and wherein the method further comprises:

aligning the post-weld image data and the epoxy image data based on a reference object of the electric motor stator;

determining, in response to aligning the image data and the epoxy image data and for each pixel from among the plurality of pixels of the post-weld image data, the post-weld intensity value;

providing the digital twin to one or more convolutional layers to generate one or more feature maps; and providing the one or more feature maps to one or more pooling layers to generate a reduced image, wherein the one or more epoxy characteristics are further based on the reduced image.

18. The method of claim 12, wherein the one or more epoxy characteristics include an epoxy thickness, an epoxy distribution, or a combination thereof.

19. A system for non-destructively testing an electric motor stator, the system comprising:

one or more processors and one or more nontransitory computer-readable mediums comprising instructions that are executable by the one or more processors, wherein the instructions include:

obtaining pre-weld image data of the electric motor stator from one or more image sensors;

determining one or more pre-weld characteristics of the electric motor stator based on the pre-weld image data;

performing a welding process based on the one or more pre-weld characteristics, wherein the welding process includes welding hairpin wires and connectors of the electric motor stator;

obtaining post-weld image data of the electric motor stator in response to performing the welding process;

obtaining epoxy image data of the electric motor stator in response to obtaining the post-weld image data;

performing a difference-based image processing routine based on the post-weld image data and the epoxy image data to generate a digital twin of the electric motor stator; and determining one or more epoxy characteristics of the electric motor stator based on the digital twin, wherein the one or more epoxy characteristics include an epoxy thickness, an epoxy distribution, or a combination thereof.

20. The system of claim 19, wherein the difference-based image processing routine is one of a computer vision routine and a convolutional neural network routine.

* * * * *